United States Patent [19]

Markezich

[11] 4,005,134

[45] Jan. 25, 1977

[54] METHOD FOR MAKING AROMATIC BIS(ETHER DICARBOXYLIC ACID)

[75] Inventor: Ronald L. Markezich, Scotia, N.Y.

[73] Assignee: General Electric Company, Schenectady, N.Y.

[22] Filed: Sept. 11, 1975

[21] Appl. No.: 612,368

[52] U.S. Cl. .................... 260/520 E; 260/343.4; 260/516
[51] Int. Cl.$^2$ .................................. C07C 51/00
[58] Field of Search ............. 260/520 E, 343.4, 516

[56] References Cited
UNITED STATES PATENTS

| 3,247,208 | 4/1966 | Schenker | 260/520 E |
| 3,875,208 | 4/1975 | Cohen et al. | 260/520 E |
| 3,879,428 | 4/1975 | Heath et al. | 260/520 E |
| 3,903,101 | 9/1975 | Yoshida et al. | 260/520 E |

OTHER PUBLICATIONS

Weygand, "Prep. Org. Chem.," p. 450, John Wiley & Sons (1972).
Moller, "Chem. of Org. Comp.," 3rd. Edition, Edition, p. 604, Saunders (1965).

*Primary Examiner*—Norman Morganstern
*Attorney, Agent, or Firm*—William A. Teoli; Joseph T. Cohen; Jerome C. Squillaro

[57] ABSTRACT

A method is provided for making aromatic bis(ether dicarboxylic acid) useful for making high performance injection moldable polyetherimides. An aromatic bis(ether N-organo phthalimide) is hydrolyzed directly to the corresponding tetra-acid by heating the aromatic bis(ehter N-organo phthalimide) in a closed system in the presence of acetic acid, water, and a mineral acid.

6 Claims, No Drawings

METHOD FOR MAKING AROMATIC BIS(ETHER DICARBOXYLIC ACID)

The present invention relates to a method for making aromatic bis(ether dicarboxylic acid) by the acid hydrolysis of aromatic bis(ether N-organo phthalimide).

Prior to the present invention, as shown by U.S. Pat. No. 3,879,428 Heath et al., assigned to the same assignee as the present invention, hydrolysis of aromatic bis(ether phthalimide) was accomplished in the presence of base to produce a tetraacid salt which required further acidification to produce the corresponding aromatic bis(ether dicarboxylic acid). The aromatic bis(-dicarboxylic acid) can be converted readily to the corresponding aromatic bis(ether anhydride), or can be coreacted with organic diamine as shown, for example, by Takekoshi et al. U.S. Pat. No. 3,833,546 to produce injection moldable polyetherimides, which patent is also assigned to the same assignee as the present invention. It would be desirable to be able to produce aromatic bis(ether dicarboxylic acid)s by a more direct route without the employment of a base hydrolysis step followed by an acidification step.

The present invention is based on the discovery that aromatic bis(ether N-organo phthalimide)s can be directly hydrolyzed to the corresponding tetraacid without resort to a base hydrolysis step, if the aforementioned bisimide is heated in a closed system with a mixture of water, acetic acid and a mineral acid.

There is provided by the present invention, a method for making an aromatic bis(ether dicarboxylic acid) based on the hydrolysis of an aromatic bis(ether N-organo phthalimide) which involves the improvement comprising heating a mixture of aromatic bis(ether N-organo phthalimide), acetic acid, water, and mineral acid is a closed system to a temperature in the range of between about 80° to 200° C where there is utilized from about 3 to 35% by weight of bis(ether N-organo phthalimide) based on the weight of reaction mixture, and the mineral acid is used at a concentration sufficient to provide from 2 to 8 moles of mineral acid per mole of bisimide, whereby the direct hydrolysis of the aromatic bis(ether N-organo phthalimide) is achieved without resort to a base hydrolysis step and the acidification of the resulting tetraacid salt.

Included by the aromatic bis(ether N-organo phthalimide)s, hereinafter referred to as "bisimide" are compounds shown by the following formula

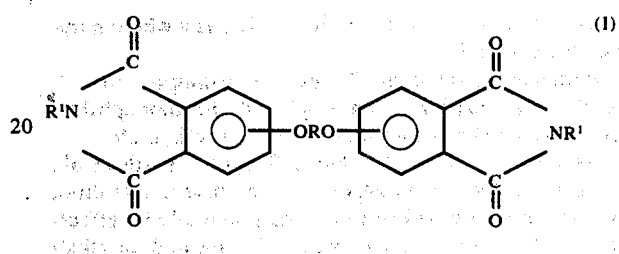

where R is a divalent aromatic radical having from 6–30 carbon atoms and $R^1$ is a monovalent organo radical selected from the class consisting of $C_{(1-8)}$ alkyl radicals and organic radicals having from 6–20 carbon atoms selected from the class consisting of aromatic hydrocarbon radicals and halogenated derivatives thereof.

Radicals included by R are, more particularly,

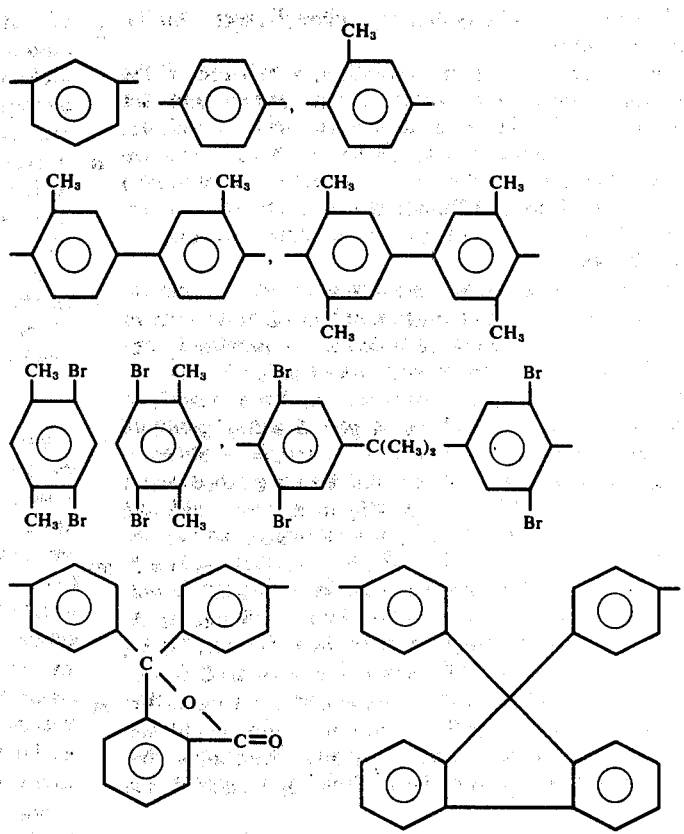

and divalent organic radicals of the general formula

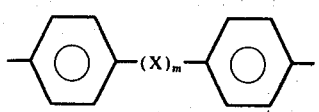

where X is a member selected from the class consisting of divalent radicals of the formula, $-C_yH_{2y}-$,

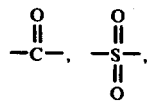

—O—, and —S—, where $m$ is 0 or 1, $y$ is a whole number from 1 to 5.

Radicals included by $R^1$ are, for example, phenyl, tolyl, xylyl, naphthyl, chlorophenyl, bromonaphthyl, etc., and alkyl radicals such as methyl, ethyl, etc.

As shown by U.S. Pat. No. 3,879,428 Heath et al., assigned to the same assignee as the present invention, the above mentioned bisimides can be made by effecting reaction between a nitrophthalimide and an alkali diphenoxide. Typical of the bisimides which can be hydrolyzed in accordance with the practice of the invention are, for example 2,2-bis[4-(3,4-dicarboxyphenoxy)-phenyl] propane bis(N-methylimide), 2,2-bis[4-(3,4-dicarboxyphenoxy)-phenyl]propane bis(N-phenylimide), bis[4-(3,4-dicarboxyphenoxy)-phenyl]methane bis(N-methylimide), bis[4-(3,4-dicarboxyphenoxy)-phenyl]ether bis(N-methylimide).

In the practice of the invention, a mixture of the bisimide, acetic acid, water, and a mineral acid, for example, hydrochloric acid, sulfuric acid, phosphoric acid, etc., is charged to a reactor, such as a pressure vessel. The pressure vessel can thereafter be immersed in an oil bath to heat the mixture whereby the conversion of the bisimide to the corresponding tetraacid can be effected.

Experience has shown that unless the mineral acid is utilized within a concentration of from 2 to 8 moles of mineral acid, per mole of bisimide, as previously defined, either complete conversion of imide functionality to carboxylic functionality will not be achieved, or cleavage can occur, such as the gem-dimethyl group of the BPA moiety to produce, for example, 4-phenoxyphthalic acid. It has been found that a proportion of from about 1 part to 20 parts of glacial acetic acid and of from about 1 part to 10 parts of water, per part of bisimide will provide for effective results, although smaller and larger amounts can be utilized without adversely affecting the overall yield of the tetraacid. A temperature in the range of from about 80° to 220° C, and preferably from 120° to 160° C can be used. Agitation of the mixture, such as by use of a stirrer in the reaction vessel, or by the agitation of the vessel can facilitate the course of the reaction. Preferably, the bisimide is used at from 10 to 30% by weight of the mixture.

Depending upon such factors as the nature of the bisimide hydrolyzed, the degree of agitation, the temperature employed, etc., a reaction period of from 10 hours to 100 hours or more to as little as 1 hour to 10 hours or less will not be unusual. Preferably, concentrated hydrochloric acid or concentrated sulfuric acid can be employed. However, in most instances, phosphoric acid, $H_3PO_4$, also can be effectively utilized as the mineral acid.

Recovery of the tetraacid can be readily effected by allowing the reactor to cool and pouring the contents into water which has been slightly acidified with a mineral acid such as hydrochloric acid. The resulting mixture can thereafter be stirred and refluxed for periods of up to 60 minutes or more to allow the tetraacid to solidify. Recovery of the final tetraacid product can be readily achieved by standard filtration or gravity separation techniques such as centrifuging, decantation, etc. The final product can thereafter be dried in air, if desired.

The tetraacid made in accordance with the practice of the invention can thereafter be converted to the corresponding aromatic bis(ether dianhydride) or can be directly utilized to make polyetherimide by procedures involving the employment of organic diamine, organic diisocyanate, etc., as previously taught.

In order that those skilled in the art will be better able to practice the invention, the following examples are given by way of illustration and not by way of limitation. All parts are by weight.

EXAMPLE 1

A mixture was placed in a pressure vessel equipped with a stirrer consisting of 21.21 parts of 2,2-bis[4-(3'4'-di-carboxyphenoxy)phenyl]propane bis(N-methylimide), 84 parts of glacial acetic acid, 40 parts of water and sufficient parts of concentrated hydrochloric acid to provide a ratio of 6.2 moles of HCl, per mole of bisimide. The mixture was stirred and heated at a temperature of 160° C for 16 hours. The mixture was then allowed to cool and poured into 2,000 parts of 1N hydrochloric acid. The mixture was heated to reflux with stirring for 60 minutes. The mixture was then allowed to cool to room temperature and 19.93 parts of a tan solid was obtained. Based on the method of preparation, proton and $^{13}C$ nmr spectra, and infra-red spectra, the solid was 2,2-bis[4-(3',4'-dicarboxyphenoxy)phenyl]propane which was obtained in a 92% yield and at a purity greater than 99%.

EXAMPLE 2

The above procedure was repeated several times except the concentration of the hydrochloric acid was varied in the mixture over range of from about 4.4 moles to 24 moles of HCl, per mole of bisimide to determine whether the mole ratio of HCl/Bisimide was critical with respect to yield of tetraacid. A decrease in yield of the aromatic bis(ether acid) could be based on either cleavage at the gem-dimethyl group of the BPA moiety, or in some instances reduced conversion of imide units to carboxylic acid units. The temperature was also varied over a range of between 120° to 160° C to determine the conditions for optimum yield. The following table shows the results obtained where "Time" indicates reaction time, T indicates the temperature in ° C of the oil bath used to heat the reactor, "HCl/BI" is the value obtained by dividing moles of HCl by moles of Bisimide in the reaction mixture and "% Yield" is the yield of tetraacid.

| Ex. | Time (hrs) | Temp (° C) | HCl/BI | % Yield |
|-----|------------|------------|--------|---------|
| 2 | 16 | 155° | 6.8 | 96 |
| 3 | 93 | 120° | 6 | 84 |
| 4 | 15.5 | 160° | 9.2 | 66 |
| 5 | 5 | 160° | 3.2 | 80 |
| 6 | 16 | 160° | 1.0 | 38 |

As shown by the above results, maximum yield was obtained at an HCl/BI ratio having a value within the definition of the present invention. When a temperature of 160° C at 15.5 hours was used utilizing a concentration of HCl sufficient to provide an HCl/BI value of 9.2, the yield of tetraacid was only 66 percent, due to a 34 percent loss of product as a result of cleavage at the gem-dimethyl group.

EXAMPLE 7

A sealed pressure vessel containing 24 parts of the bisimide of Example 1, 84 parts of glacial acetic acid, 50 parts of water and 1.84 parts of concentrated sulfuric acid was immersed in an oil bath. The vessel was heated for 8.25 hours at 160° C, while the mixture was agitated. Sufficient sulfuric acid was used to provide an $H_2SO_4/Bi$ ratio of about 4. The mixture was allowed to cool to room temperature. A solid crystallized out of the solution. After filtration and drying, there was obtained a 78% yield of a tan solid product. Based on method of preparation and proton NMR analysis, the product was 2,2-bis[4-(3'4'-dicarboxyphenoxy)phenyl] propane. The above procedure was repeated except that sulfuric acid was used at a concentration to produce an $H_2SO_4/Bi$ ratio having a value of 24. Although the mixture was heated 16.5 hours at a temperature of 155° C, the yield of tetra acid was about 30% as a result of cleavage at the gem-dimethyl group of the BPA moiety to give 4-phenoxyphthalic acid.

Although the above results are limited to only a few of the very many variables which can be used in the practice of the invention, it should be understood the method of the present invention.

What I claim as new and desire to secure by Letters Patent of the United States is:

1. In a method for making an aromatic bis(ether dicarboxylic acid) based on the hydrolysis of an aromatic bis(ether N-organophthalimide), the improvement which comprises heating a mixture of aromatic bis(ether N-organophthalimide, acetic acid, water and mineral acid in a closed system at a temperature in the range between about 80° C to 200° C, where the mineral acid is used in the mixture at a concentration sufficient to provide from 2 to 8 moles of mineral acid per mole of bisimide and there is utilized a proportion by weight of from about 1 part to 20 parts of glacial acetic acid and from about 1 part to 10 parts of water per part of bisimide which is used in the mixture in a proportion of from 10% by weight to 30% by weight, whereby the direct hydrolysis of the aromatic bis(ether N-organophthalimide) is achieved without resort to a base hydrolysis step followed by acidification of the resulting tetraacid salts.

2. A method in accordance with claim 1, where the aromatic bis(ether N-organophthalimide) is 2,2-bis[4-(3',4'-dicarboxyphenoxy)phenyl] propane, bis(N-methyl imide).

3. A method in accordance with claim 1, where the mineral acid is hydrochloric acid.

4. A method in accordance with claim 1, where the mineral acid is sulfuric acid.

5. A method in accordance with claim 1, where the mineral acid is phosphoric acid.

6. A method in accordance with claim 1, where the mixture is heated at a temperature within the range of between 120° to 160° C.

* * * * *